United States Patent
Green et al.

(10) Patent No.: US 6,303,303 B1
(45) Date of Patent: Oct. 16, 2001

(54) METHOD AND SYSTEM FOR DNA SEQUENCE DETERMINATION AND MUTATION DETECTION

(75) Inventors: Ronald J. Green, Toronto; Vrijmoed Chi, Mississauga; Rodney D. Gilchrist, Oakville; Gregory Dee; John K. Stevens, both of Toronto, all of (CA)

(73) Assignee: Visible Genetics Inc, Toronto (CA)

( * ) Notice: Subject to any disclaimer, the term of this patent is extended or adjusted under 35 U.S.C. 154(b) by 0 days.

(21) Appl. No.: 09/190,756

(22) Filed: Nov. 12, 1998

Related U.S. Application Data

(62) Division of application No. 08/497,202, filed on Jun. 30, 1995, now Pat. No. 5,853,979.

(51) Int. Cl.[7] .................................................. C12Q 1/68
(52) U.S. Cl. ............................................. 435/6; 435/91.2
(58) Field of Search .......................................... 435/6, 91.2

(56) References Cited

U.S. PATENT DOCUMENTS

| | | |
|---|---|---|
| 3,742,202 | 6/1973 | Spreitzhofer ........................ 235/183 |
| 4,720,786 | 1/1988 | Hara . |
| 4,811,218 | 3/1989 | Hunkapiller et al. ........... 364/413.01 |
| 4,941,092 | 7/1990 | Hara . |
| 4,960,999 | 10/1990 | McKean et al. .................. 250/461.1 |
| 4,982,326 | 1/1991 | Kaneko . |
| 5,108,179 | 4/1992 | Myers ................................. 356/344 |
| 5,119,316 | 6/1992 | Dam et al. ........................... 364/498 |
| 5,190,632 | 3/1993 | Fujimiya et al. ................ 204/299 R |
| 5,213,673 | 5/1993 | Fujimiya et al. ................ 204/299 R |
| 5,246,866 | 9/1993 | Nasu et al. ............................. 436/94 |
| 5,273,632 | 12/1993 | Stockham . |
| 5,308,751 | 5/1994 | Ohkawa et al. . |
| 5,365,455 | 11/1994 | Tibbetts et al. ...................... 364/497 |
| 5,419,825 | 5/1995 | Fujii ..................................... 204/299 |
| 5,502,773 | 3/1996 | Tibbetts et al. ...................... 382/129 |

FOREIGN PATENT DOCUMENTS

| | | |
|---|---|---|
| 4405251 | 8/1994 | (DE) . |
| 0592060 | 4/1994 | (EP) .............................. C12Q/1/68 |
| 2225139 | 5/1990 | (GB) . |
| 9635810 | 11/1996 | (WO) . |
| WO 9741259 | 11/1997 | (WO) . |
| WO 9800708 | 1/1998 | (WO) . |
| WO 9811258 | 3/1998 | (WO) . |

OTHER PUBLICATIONS

Koutny et al., "Automated Image Analysis for Distortion Compensation in Sequencing Gel Electrophoresis" *Applied Spectroscopy* 46: 136–141 (1992).

Mayrand et al., "The use of fluorescence detection and internal lane standards to size PCR products".

Bowling et al., "Neighboring Nucleotide Interactions During DNA Sequencing Electrophoresis", *Nucleic Acids Res.* 19: 3089–3097 (1991).

Giddings et al., "An Adaptive, Object Oriented Strategy for Base calling in DNA Sequences", *Nucleic Acids Res.* 21: 4530–4540 (1993).

Golden II, et al., "Pattern Recognition for Automated DNA Sequencing: I. On–Line Signal Conditioning and Feature Extraction for Basecalling".

Tibbetts et al., "Neural Networks for Automated Basecalling of gel–Based Sequencing Ladders".

Smith et al., "Fluorescence detection of automated DNA sequence analysis", *Nature* 321: 674–679 (1986).

Dear and Staden, A sequence assembly and editing program for efficient management of large projects, Nucleic Acids Research, vol. 19, No. 14, 3907–3911, Oxford University Press, 1991.

Plaschke, Voss, Hahn, Ansorge, and Schackert, Doublex, Sequencing in Molecular Diagnosis of Hereditary Diseases, BioTechniques 24:838–841, May 1998.

*Primary Examiner*—Scott W. Houtteman
(74) *Attorney, Agent, or Firm*—Oppedahl & Larson LLP

(57) ABSTRACT

Normalization of experimental fragment patterns for nucleic acid polymers having putatively known sequences starts with obtaining at least one raw fragment pattern for the experimental sample. The raw fragment pattern represents the positions of a selected nucleic acid base within the polymer as a function of migration time or distance. This raw fragment pattern is conditioned using conventional baseline correction and noise reduction technique to yield a clean fragment pattern. The clean fragment pattern is then evaluated to determine one or more "normalization coefficients." These normalization coefficients reflect the displacement, stretching or shrinking, and rate of stretching or shrinking of the clean fragment, or segments thereof, which are necessary to obtain a suitably high degree of correlation between the clean fragment pattern and a standard fragment pattern which represents the positions of the selected nucleic acid base within a standard polymer actually having the known sequence as a function of migration time or distance. The normalization coefficients are then applied to the clean fragment pattern to produce a normalized fragment pattern which is used for base-calling in a conventional manner. This method may be implemented in an apparatus comprising a computer processor programmed to determine normalization coefficients for an experimental fragment pattern. This computer may be separate from the electrophoresis apparatus, or part of an integrated unit.

14 Claims, 8 Drawing Sheets

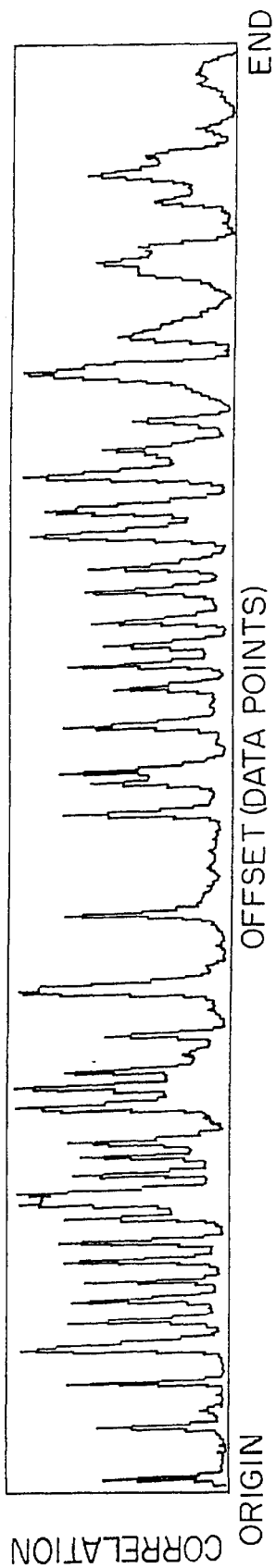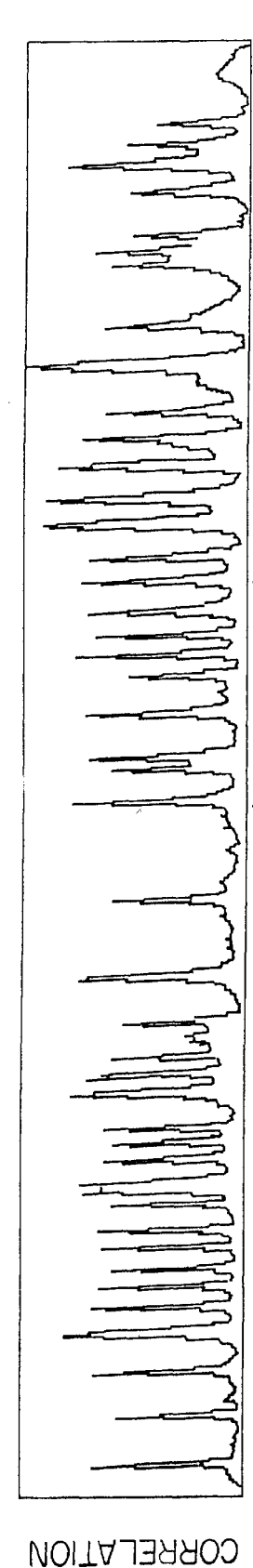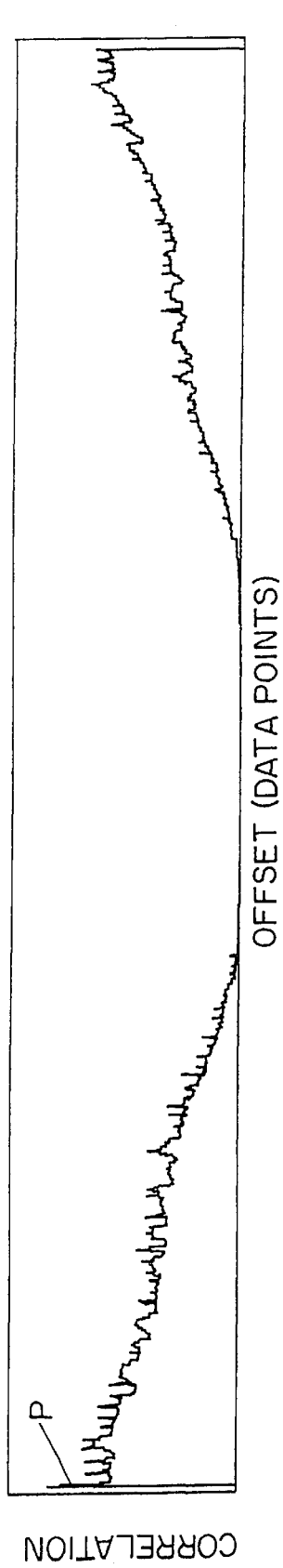

METHOD AND SYSTEM FOR DNA SEQUENCE DETERMINATION AND MUTATION DETECTION

This application is a divisional of copending U.S. patent application Ser. No. 08/497,202 filed Jun. 30, 1995 now U.S. Pat. No. 5,853,979.

BACKGROUND OF THE INVENTION

This invention relates to a method and system of nucleotide sequence determination and mutation detection in a subject nucleic acid molecule for use with automated electrophoresis detection apparatus.

One of the steps in nucleotide sequence determination of a subject nucleic acid polymer is interpretation of the pattern of oligonucleotide fragments which results from electrophoretic separation of fragments of the subject nucleic acid polymer (the "fragment pattern"). The interpretation of the fragment pattern, colloquially known as "base-calling," results in determination of the order of four nucleotide bases, A (adenine), C (cytosine), G (guanine) and T (thymine) for DNA or U (uracil) for RNA in the subject nucleic acid polymer.

In the earliest method of base-calling, a method which is still commonly employed, the subject nucleic acid polymer is labeled with a radioactive isotope and either Maxam and Gilbert chemical sequencing (Proc. Natl. Acad. Sci. USA, 74: 560–564 (1977)) or Sanger et al. chain termination sequencing (Proc. Natl. Acad. Sci. USA 74: 5463–5467 (1977)) is performed. The resulting four samples of nucleic acid fragments (terminating in A, C, G, or T(U) respectively in the Sanger et al. method) are loaded into separate loading sites at the top end of an electrophoresis gel. An electric field is applied across the gel, and the fragments migrate through the gel. During this electrophoresis, the gel acts as a separation matrix. The fragments, which in each sample are of an extended series of discrete sizes, separate into bands of discrete species in a channel along the length of the gel. Shorter fragments generally move more quickly than larger fragments. After a suitable separation period, the electrophoresis is stopped. The gel may now be exposed to radiation sensitive film for the generation of an autoradiograph. The pattern of radiation detected on the autoradiograph is a fixed representation of the fragment pattern. A researcher then manually base-calls the order of fragments from the fragment pattern by identifying the stepwise sequence of the order of bands across the four channels.

More recently, with the advent of the Human Genome Organization and its massive project to sequence the entire human genome, researchers have been turning to automated DNA sequencers to process vast amounts of DNA sequence information. Existing automated DNA sequencers are available from Applied Biosystems, Inc. (Foster City, Calif.), Pharmacia Biotech, Inc. (Piscataway, N.J.), Li-Cor, Inc. (Lincoln, Nebr.), Molecular Dynamics, Inc. (Sunnyvale, Calif.) and Visible Genetics Inc. (Toronto). Automated DNA sequencers are basically electrophoresis apparatuses with detection systems which detect the presence of a detectable molecule as it passes through a detection zone. Each of these apparatus, therefore, are capable of real time detection of migrating bands of oligonucleotide fragments; the fragment patterns consist of a time based record of fluorescence emissions or other detectable signals from each individual electrophoresis channel. They do not require the cumbersome autoradiography methods of the earliest technologies to generate a fragment pattern.

The prior art techniques for computer-assisted base-calling for use in automated DNA sequencers are exemplified by the method of the Pharmacia A.L.F.(tm) sequencer. Oligonucleotide fragments are labeled with a fluorescent molecule such as fluorescein prior to the sequencing reactions. Sanger et al. sequencing is performed and samples are loaded into the top end of an electrophoresis gel. Under electrophoresis the bands of species separate, and a laser at the bottom end of the gel causes the fragments to fluoresce as they pass through a detection zone. The fragment patterns are a record of fluorescence emissions from each channel. In general, each fragment pattern includes a series of sharp peaks and low, flat plains; the peaks representing the passage of a band of oligonucleotide fragments; the plains representing the absence of such bands.

To perform computer-assisted base-calling, the A.L.F. system executes at least four discrete functions: 1) it smooths the raw data with a band-pass frequency filter; 2) it identifies successive maxima in each data stream; 3) it aligns the smoothed data from each of the four channels into an aligned data stream; and 4) it determines the order of the successive maxima with respect to the aligned data stream. The alignment process used in the apparatus depends on the existence of very little variability between the lanes of the gel. In this case, the fragment patterns from each lane can be superimposed by alignment to a presumed starting point in each pattern to provide a record of a continuous, non-overlapping series of sharp peaks, each peak representing a one nucleotide step in the subject nucleic acid. Where a distinct ordering of peaks can not be made, the computer identifies the presence of ambiguities and fails to identify a sequence.

Other published methods of computer-assisted base-calling include the methods disclosed by Tibbetts and Bowling (U.S. Pat. No. 5,365,455) and Dam et al (U.S. Pat. No. 5,119,316) which patents are incorporated herein by reference. Tibbetts and Bowling disclose a method and system which relies on the second derivative of the peak slopes to smooth the data. The second derivative is used to provide an informative variable and an intensity variable to determine the nucleic acid sequence corresponding to the subject nucleic acid polymer. Dam et al. disclose a method of combining peak shapes from two signal spectrums derived from the same electrophoresis channel to determine the order of nucleotides in the subject nucleic acid polymer.

Three practical problems face all existing methods and systems of base-calling. The first is the inability to align shifted lanes of data. If the signal from the related data streams does not begin at approximately the same time, it is difficult, if not impossible, for these techniques to determine the correct alignment. Secondly, it is a challenge to resolve "compressions" in the fragment pattern: those anomalies wherein the signal from two or more nucleotides in a row are not distinguishably separated as compared to other nucleotides in the general vicinity. Compressions result most often from short hairpin loops at the end of a fragment which cause altered gel mobility features. The third problem is the inability to identify nucleotide sequences beyond the limits of single nucleotide resolution. Larger fragments tend to need longer electrophoresis runs to separate into discrete bands of fragments, in part because a one nucleotide addition to a 300 nt fragment is less significant than a one nucleotide addition to a 25 nt fragment. The limit of resolution is reached when individual bands can not be usefully distinguished.

All of these problems limit the most crucial aspects of base-calling, which are speed, read-length and accuracy. Read-length is the number of fragment bands which can be identified from the fragment pattern. Greater read-length provides greater information about the DNA sequence in question. Accuracy measures the number of base-calling errors. Frequent errors are unacceptable since they alter the biological meaning of the DNA sequence in question. And, as described below, if DNA sequence determination is to be used as a tool for diagnostic purposes, base-calling errors can lead to misdiagnosis.

The advent of DNA sequence-based diagnosis provides new opportunities for improved speed, accuracy and read-length in computer-assisted base-calling. DNA sequence-based diagnosis is the routine sequencing of patient DNA to identify genotype and/or specific gene sequences of the patient, wherein the DNA sequence is reported back to the physician and patient in order to assist in diagnosis and treatment of patient conditions. One of the great advantages of DNA sequence-based diagnosis is that the DNA sequence being examined is largely known. As demonstrated by the instant invention, it is possible to use the known fragment pattern for each DNA sequence to assist in the interpretation of the fragment pattern obtained from a patient sample to obtain improved read-length and accuracy. It can also be used to increase the speed of sample analysis.

It is an object of the instant invention to provide a method and system for nucleotide sequence determination and mutation detection which can be used with DNA sequence-based diagnosis.

It is a further object of the instant invention to provide a method and system for nucleotide sequence determination and mutation detection when the fragment pattern demonstrates localized compressions.

It is a further object of the instant invention to provide a method and system for nucleotide sequence determination and mutation detection when the fragment pattern does not provide single nucleotide resolution.

It is a further object of the instant invention to provide a method and system of computer-assisted base-calling which can be used with fragment pattern records from high speed electrophoretic separations which demonstrate less than ideal separation characteristics.

SUMMARY OF THE INVENTION

These and other objects of the invention are realized by the application of a novel approach to the normalization of experimental fragment patterns for nucleic acid polymers having putatively known sequences. In this method, at least one raw fragment pattern is obtained for the experimental sample. The raw fragment pattern represents the positions of a selected nucleic acid base within the polymer as a function of migration time or distance. This raw fragment pattern is conditioned using conventional baseline correction and noise reduction technique to yield a clean fragment pattern. The clean fragment pattern is then evaluated to determine one or more "normalization coefficients." These normalization coefficients reflect the displacement, stretching or shrinking, and rate of stretching or shrinking of the clean fragment, or segments thereof, which are necessary to obtain a suitably high degree of correlation between the clean fragment pattern and a standard fragment pattern which represents the positions of the selected nucleic acid base within a standard polymer actually having the known sequence as a function of migration time or distance. The normalization coefficients are then applied to the clean fragment pattern to produce a normalized fragment pattern which is used for base-calling in a conventional manner.

In applying the present invention to the evaluation of nucleic acid polymers of putatively known sequence to the detection of well-characterized mutations in which one base is substituted for another at a constant site in the gene, it will generally be sufficient to determine normalization coefficients for a single fragment pattern reflecting the positions of either the normal or mutant base within the nucleic acid polymer. For more general applications, however, it is desirable to determine separate normalization coefficients for each of the four oligonucleotide fragment patterns obtained for the sample by correlating them with four standard fragment patterns.

The method of the invention is advantageously implemented in an apparatus comprising a computer processor programmed to determine normalization coefficients for an experimental fragment pattern. This computer may be separate from the electrophoresis apparatus, or part of an integrated unit.

BRIEF DESCRIPTION OF THE DRAWINGS

FIGS. 2A, 2B, and 2C illustrates the correlation method of instant invention.

DETAILED DESCRIPTION OF THE INVENTION

Figure 1:
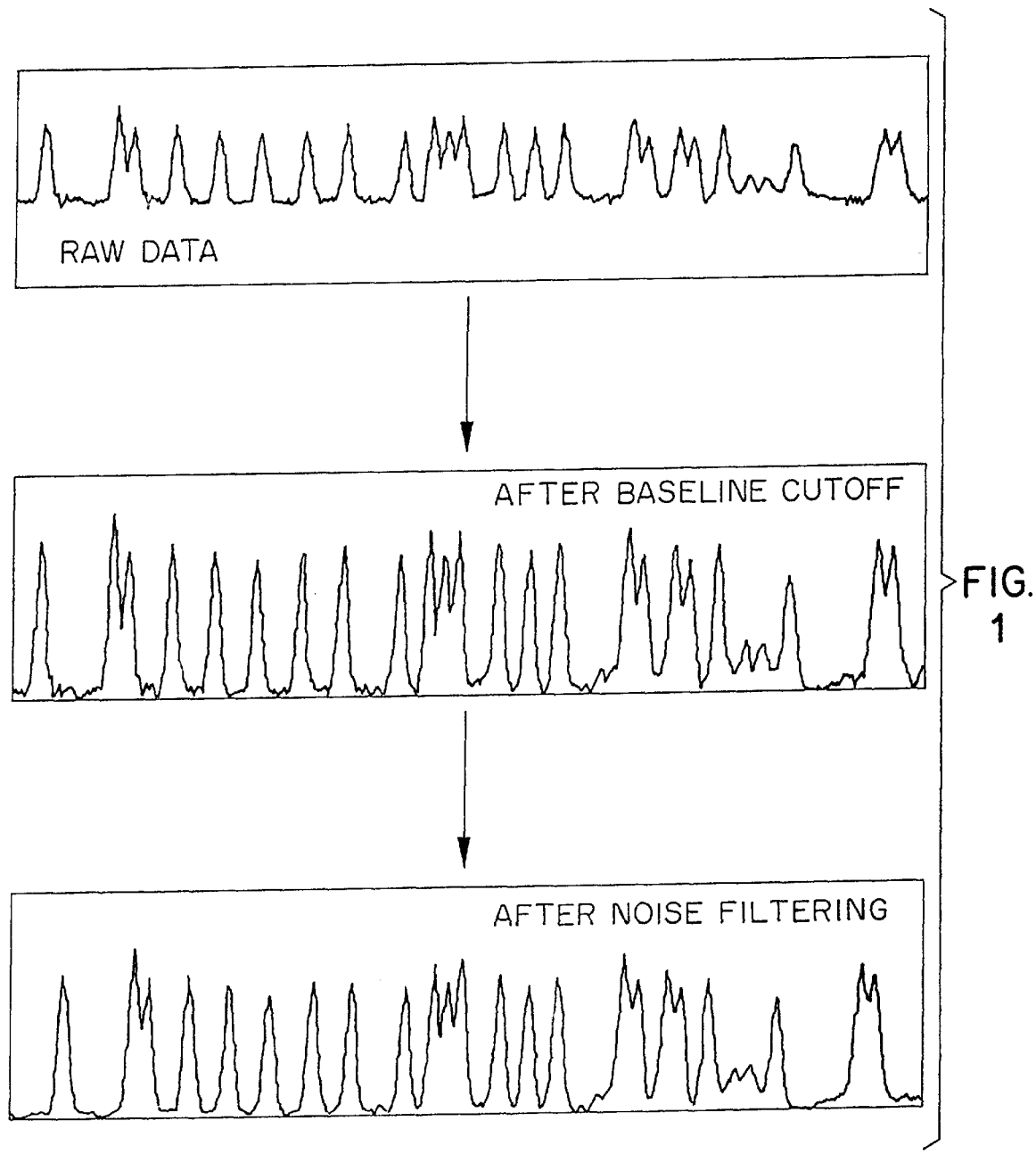
FIG. 1 illustrates the effect of background subtraction and band-pass frequency filtration on the appearance of data.

The instant invention is designed to work with DNA sequence-based diagnosis or any other sequencing environment involving nucleotide sequence determination and/or mutation detection for the same region of DNA in a plurality of individual DNA-containing samples (human or otherwise). This "diagnostic environment" is unlike the vast majority of DNA sequence determination now occurring in which researchers are attempting to make an initial determination of the nucleotide sequence of unknown regions of DNA. DNA sequence-based diagnosis in which the DNA sequence of a patient gene is determined is one example of a technique performed within a diagnostic environment to which the present invention is applicable. Other examples include identification of pathogenic bacteria or viruses, DNA fingerprinting, plant and animal identification, etc.

The present invention provides a method for normalization of experimental fragment patterns for nucleic acid polymers with putatively known sequences which enhances the ability to interpret the information found in the fragment patterns. In this method, at least one raw fragment pattern is obtained for the experimental sample. As used in the specification and claims hereof, the term "raw fragment pattern" refers to a data set representing the positions of one selected nucleic acid base within the experimental polymer as a function of migration time or distance. Preferred raw fragment patterns which may be processed using the present invention include raw data collected using the fluorescence detection apparatus of automated DNA sequencers. However, the present invention is applicable to any data set which reflects the separation of oligonucleotide fragments in space or time, including real time fragment patterns using any type of detector, for example a polarization detector as described in U.S. patent application Ser.No. 08/387,272 filed Feb. 13, 1995 (now U.S. Pat. No. 5,543,081) and incorporated herein by reference; densitometer traces of autoradiographs or stained gels; traces from laser-scanned gels containing fluorescently-tagged oligonucleotides; and fragment patterns from samples separated by mass spectrometry.

This raw fragment pattern is conditioned, for example using conventional baseline correction and noise reduction techniques to yield a "clean fragment pattern." As is known in the art, three methods of signal processing commonly used are background subtraction, low frequency filtration and high frequency filtration.

Background subtraction eliminates the minimum constant noise recorded by the detector. The background is calculated as a measure of the minimum signal obtained over a selected number of data points. This measure differs from low frequency filtration which eliminates low period variations in signal that may result from variable laser intensity, etc.

High frequency filtration eliminates the small variations in signal intensity that occur over highly localized areas of signal. The result after base-line subtraction is a band-pass filter applied to the frequency domain:

$$F(f)=e^{-f^2/\sigma_2}(1-e^{-f^2/\omega_2})$$

where ω determines the low-frequency cutoff, and σ determines the high frequency cutoff, respectively. FIG. 1 illustrates the effect of background subtraction, low and high frequency filtration on the appearance of data from a Visible Genetics MICROGENE BLASTER™, resulting in a clean fragment pattern useful in the invention.

In accordance with the present invention, a "clean fragment pattern" may be obtained by the application of these signal-processing techniques singly or in any combination. In addition, other signal processing techniques may be employed to obtain comparable clean fragment patterns without departing from the present invention.

One note of caution concerning this conditioning step is the finding that signal conditioning or pre-processing may delete features of consequence in the preparation of the clean fragment pattern. It is possible to include a feedback mechanism in the system which adjusts the parameters of the filter mechanisms, based on the analysis of the degree of correlation, described below. The feedback mechanism adjusts the types of filters employed in signal processing to provide the maximum information about the subject nucleic acid sequence.

The next step in the method of the present invention is the comparison of the clean fragment pattern with a standard fragment pattern to determine one or more "normalization coefficients." The use of a "standard fragment pattern" takes advantage of the fact that in a diagnostic environment, there is a known fragment pattern that is expected from each test sample. As used in the specification and claims of this application, the term "standard fragment pattern" refers to a typical fragment pattern which results from sequencing a particular known region of DNA using the same technique as the experimental technique being employed. Thus, a standard fragment pattern may be a time-based fluorescence emission record as obtained from an automated DNA sequencer, or it may be another representation of the separated fragment pattern.

A standard fragment pattern used in the present invention includes all the less-than-ideal characteristics of nucleotide separation that may be associated with sequencing of any particular region of DNA. A standard fragment pattern may also tend to be idiosyncratic with the electrophoresis apparatus employed, the reaction conditions employed in sequencing and other factors. FIG. 2A illustrates a standard fragment pattern for the T lane of the first 260 nucleotides from the universal primer of pUC18 prepared using Sequenase 2.0 (United States Biochemical, Cleveland) and detected on a Visible Genetics MICROGENE BLASTER™. Four standard fragment patterns, one for each nucleotide, makes up the standard fragment pattern set for a particular nucleic acid polymer.

A standard fragment pattern or fragment pattern set for a particular nucleic acid polymer may be generated by various methods. One such method is to obtain several to several hundred actual fragment patterns for the DNA sequence in question from samples wherein the DNA sequence is already known. From these trial runs, a human operator may select the trial run that is found to be the most typical fragment pattern. Because of slight gel or sample anomalies, and other anomalies, different fragment patterns may have slightly different separation characteristics, and slightly different peak amplitudes etc. The selected pattern generally should not show discrete peaks in an area where compressions and overlaps are regularly found. Similarly, the selected pattern generally must not,show discrete separation of bases beyond the average single nucleotide resolution limit of the electrophoresis instrument used. An alternative method to select a standard fragment pattern is to generate a mathematically averaged result from a combination of the trial runs.

As described below, the main use of the standard fragment pattern is as a basis for modifying and normalizing an experimental fragment pattern to enhance the reliability of the interpretation of the experimental data. Thus, the standard fragment pattern is not used as a comparator for identifying deviations from the expected or "normal" sequence, and in fact is used in a manner which assumes that the experimental sequence will conform to the expected sequence.

A feature of the standard fragment pattern which is important for some uses is that it results in a minimum of (and preferably no) ambiguities in base-calling when combined with the standard fragment patterns from the three other sequencing channels. The human operator may prefer to empirically determine which fragment patterns from which lanes work best together in order to determine the standard fragment patterns for each sequencing lane.

Additionally, it is well known in the art that a range of alleles for any gene may be present in a population. To be most useful, a standard fragment pattern should result from sequencing the dominant allele of a given population. Because of this, for some applications of the invention, multiple standard fragment patterns may exist for a specific gene, even within a single experimental environment.

A standard fragment pattern may be used in different ways to provide improved read-length, accuracy and speed of sample analysis. These improvements rely on comparison of an experimental sample fragment pattern with the standard fragment pattern to determine one or more "normalization coefficients" for the particular experimental fragment pattern.

The normalization coefficients reflect the displacement, stretching or shrinking, and rate of stretching or shrinking of the clean fragment pattern, or segments thereof, which are necessary to obtain a suitably high degree of correlation between the clean fragment pattern and a standard fragment pattern which represents the positions of the selected nucleic acid base within a standard polymer actually having the known sequence as a function of migration time or distance. The normalization coefficients are then applied to the clean fragment pattern to produce a normalized fragment pattern which is used for base-calling in a conventional manner.

The process of comparing the clean fragment pattern and the standard fragment pattern to arrive at normalization coefficients can be carried out in any number of ways without departing from the present invention. In general, suitable processes involve consideration of a number of trial normalizations, and selection of the trial normalization which achieves the best fit in the model being employed. Several, non-limiting examples of useful comparison procedures are set forth below. The procedures result in the development of normalization coefficients which, when applied to an experimental fragment pattern, shift, stretch or shrink the experimental fragment pattern to achieve a high degree of overlap with the standard fragment pattern.

It will be understood, that the theoretical goal of achieving an exact overlap between an experimental fragment pattern and a standard fragment pattern may not be realistically achievable in practice, nor are repetitive and time consuming calculations to obtain perfect normalization necessary to the successful use of the invention. Thus, the term "high degree of overlap" refers to the maximization of the normalization which is achievable within practical constraints. As a general rule, a point-for-point correlation coefficient calculated for normalized fragment patterns and the corresponding standard fragment pattern of at least 0.8 is desirable, while a correlation coefficient of at least 0.95 is preferred.

FIG. 2 illustrates one correlation method of instant invention. FIG. 2A illustrates a clean fragment pattern obtained using a Visible Genetics MICROGENE BLASTER™. The signal records the T lane of a pUC18 sequencing run over the first 260 nucleotides (nt) of the subject nucleic acid molecule. The Y axis is an arbitrary representation of signal intensity; the X axis represents a time of 0 to 5 minutes. In the sequencing run shown, the peaks are cleanly separated.

FIG. 2B represents the standard fragment pattern for the T lane of the first 260 nucleotides from the universal primer of pUC18 prepared using Sequenase 2.0 (United States Biochemical, Cleveland) and detected on a Visible Genetics MICROGENE BLASTER™. The standard sequence was selected by a human operator as the most typical fragment pattern from 25 trial runs.

The experimental fragment pattern of FIG. 2A may be compared with the standard fragment pattern of FIG. 2B according to the equation:

$$f(x) \circ g(x) = \sum_{m=0}^{M-1} f^*(m)g(x+m)$$

where f* and g* are two discrete functions, x=0,1,2, . . . , M−1, f* is the complex conjugate, and M is one less than the sum of the data points in f(x) and g(x). Alternatively, the equation may be described as

COR(11,21)

in NextStep™ programming environment, where 11 =the experimental fragment pattern, and 21 =standard fragment pattern.

FIG. 2C shows the correlation values of the entire window of Lane A against the entire window of Lane B as lane A is translated relative to lane B. (As the window is shifted, it effectively wraps around, such that the End and Origin points appear to be side by side). The result shows maximum correlation at point P which corresponds to a preferred correlation shift of +40 data points.

FIG. 2 illustrates comparison of a complete experimental fragment pattern and a complete standard fragment pattern. In this case, the only normalization coefficient determined is the shift which results in the highest level of correlation. This simple model, however, lacks the robustness which is needed for general applicability. Thus for most purposes, a more complex analysis is required to obtain good normalization.

One way to take in to account the experimental variability in migration rate caused by inconsistency of sample preparation chemistry, sample loading, gel material, gel thickness, electric field density, clamping/securing of gel in instrument, detection rate and other aspects of the electrophoresis process is to assign the data points of the clean fragment pattern to one or more segments or "windows." Each window includes an empirically determined number of data points, generally in the range of 100 to 10000 data points. Windows may be of variable size within a given data series, if desired. The starting data point of each window is designated Origin; the final data point in a window is designated End. Each window of the experimental fragment pattern is then compared with a comparable number of data points making up the standard fragment using the same procedure described above.

Figure 3A:
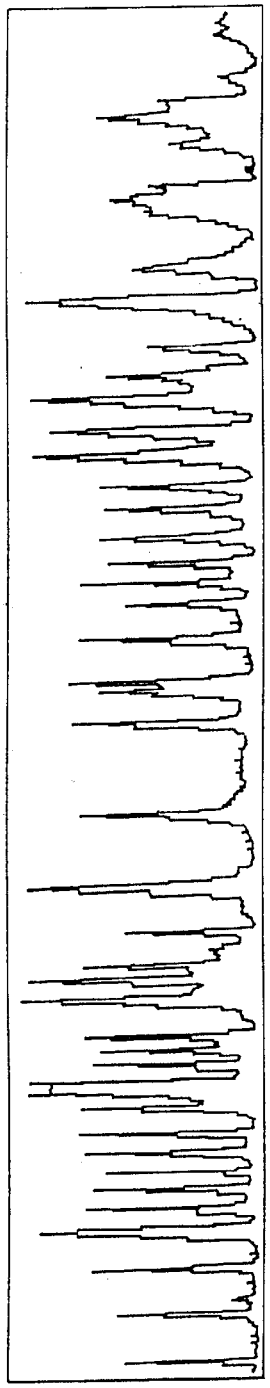
FIGS. 3A, 3B and 3C illustrate the effect of increasing the number of segments into which the sample data is divided.
Figure 3B:
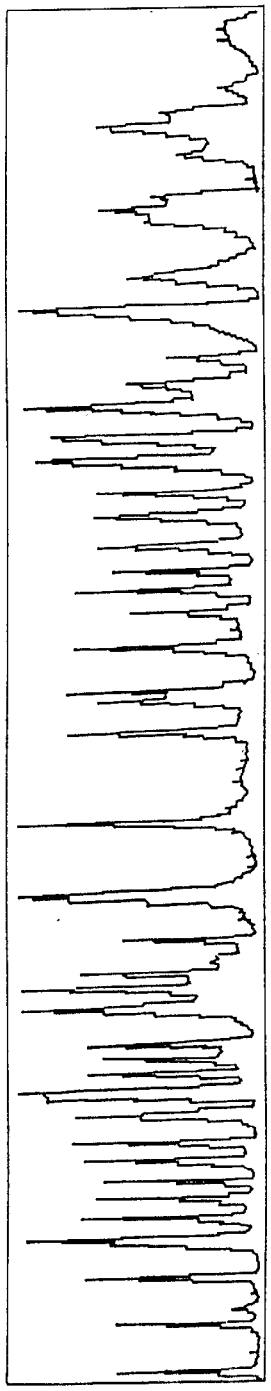

FIGS. 3A and 3B illustrate the effect of increasing the number of segments or windows into which the experimental data is divided. In FIG. 3A, the experimental fragment pattern from FIG. 2A was divided into three windows, and each was evaluated individually. Instead of the single offset of +40 data points found using a single window, the use of three windows results in an increasing degree of shift throughout the run, i,e., +24,+34 and +50 in the successive windows reading from right to left. FIG. 3B shows the use of five windows on the same experimental fragment, and results in even clearer resolution, with successive shifts of +16,+23,+35,+48, and +51 for the windows. Simply put, the consequence of too few windows is a lack of precision in shifting information. This may cause problems in base-calling aligned data. It is therefore desirable to use more than one window in the correlation process.

Figure 3C:
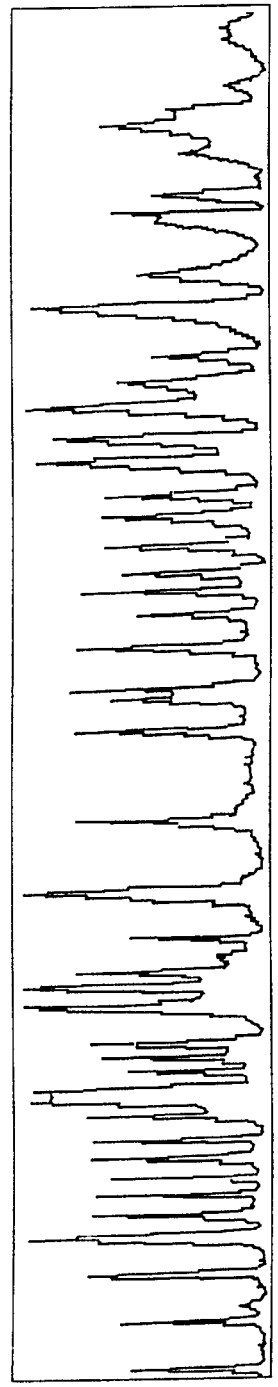
Figure 4:
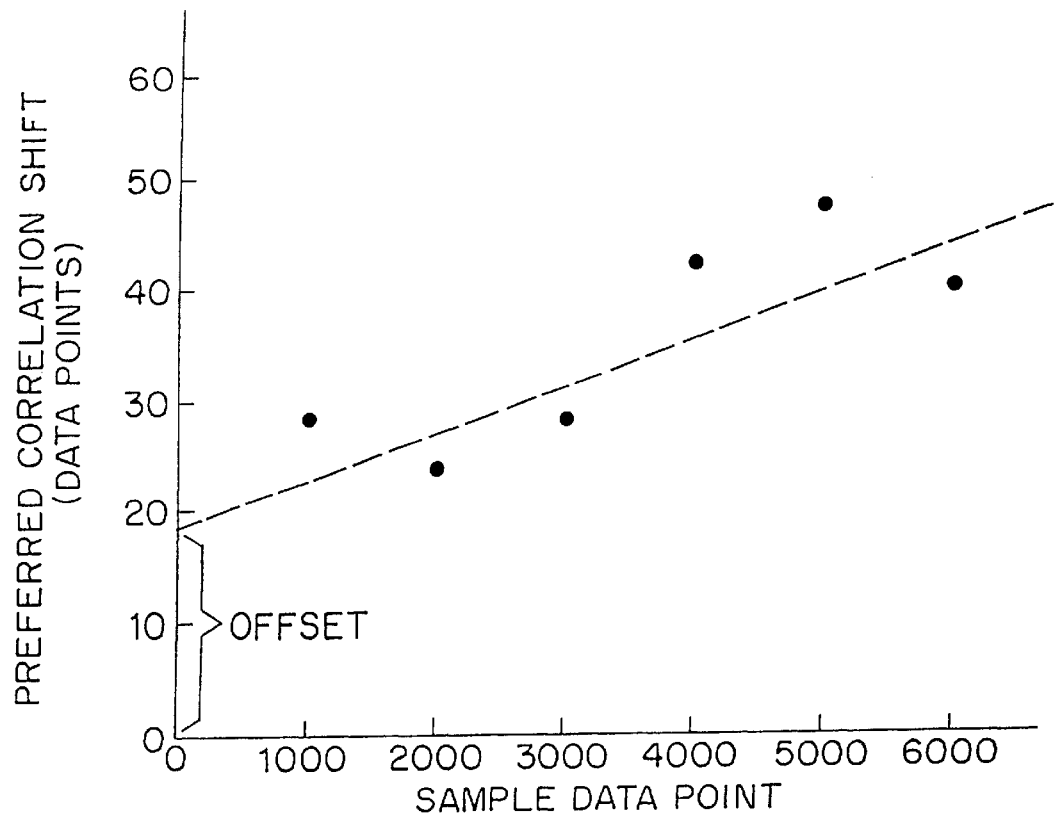
FIG. 4 is a plot of preferred correlation shift against data point number.

When more than one window is used in the analysis as illustrated in FIG. 3, it may become necessary to stretch or shrink some windows to obtain a continuous stream of data in the correlated data and to obtain a sufficiently high correlation. To calculate stretch or shrink ("elasticity") for a window where a plurality of windows are defined, one can use an "elasticity plot" of preferred correlation shift against data point number (FIG. 4). An increased number of windows increases the number of points on the elasticity plot, allowing more accurate determination of the slope and offset of the alignment line.

It has been found experimentally that in an elasticity plot, a linear equation representing the least mean square fit adequately represents the data. In this case the linear equation f(x)=mx+b will satisfy the line, where m is the slope of the line and b is the Y intercept ("offset") expressed in number of data points. The equation of the line is used to shift the sample data where the value at shifted (i) of the shifted data is given by:

shifted (i)=sample (i)+((sample (i) * m)+b)

Figure 5A:
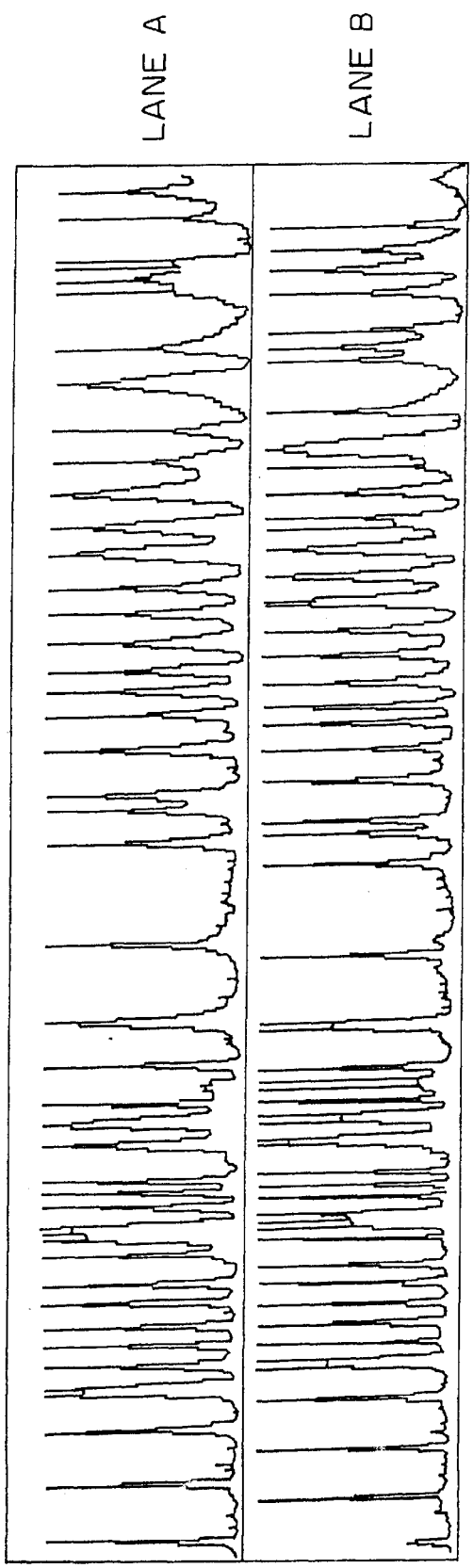
FIGS. 5A and 5B illustrate alignment of data windows.
Figure 5B:
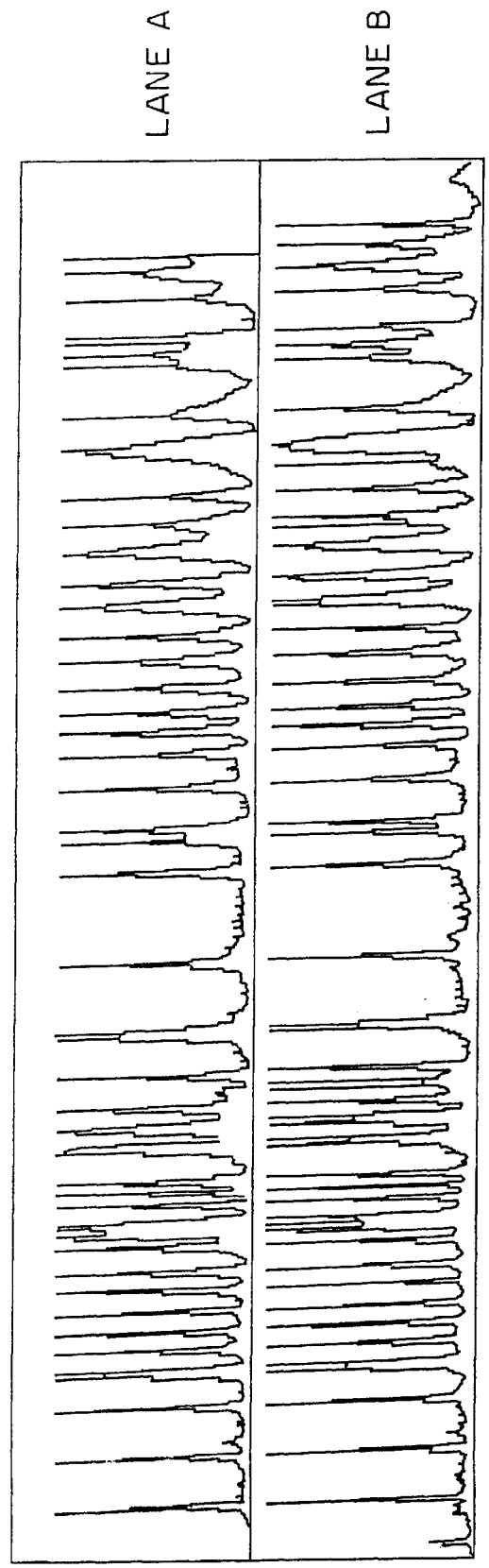

Note that as illustrated in FIG. 5 when the peaks identified in the sample window (Lane B) do not align with the standard data (Lane A), (FIG. 5A) they may be aligned for analysis purposes by padding the elastically shifted data with zeros when the formula produces values outside of the sample data's range (FIG. 5B).

While the use of multiple windows increases the accuracy of the alignment, a potential problem arises when too many windows are used. As illustrated in FIG. 3C, when windows include too few features, the correlation between the data and the window and the standard fragment pattern becomes meaningless. In FIG. 3C, window size has dropped below 1000 data points. One window which includes a single peak is found to have highest correlation with a peak distantly removed from the location where it would otherwise be expected to correlate. This situation demonstrates that the human operator must be sensitive to the unique circumstances of each standard fragment pattern to determine the optimum number of data points per window.

One method wherein windows with fewer data points can be employed is to limit the amount of the standard fragment pattern against which the window is correlated. Again, such a limitation would be empirically determined as in the other data filters employed. It is found experimentally that correlation of a sample window with that region of the standard fragment pattern that falls approximately at the same number of data points from the start of signal, and includes twice as many data points as the sample window, is sufficient to obtain correlations which are not often spurious.

An alternative approach to the determination of normalization coefficients which is applicable whether the experimental fragment pattern is considered in one or several segments makes use of an adaptive computational method known as a "Genetic Algorithm." See Holland, J., *Adaptation in natural and Artificial Systems*, The University of Michigan Press (1975). Genetic Algorithms (GAs) are particularly good at solving optimization problems where traditional methods may fail. In the context of normalization of nucleic acid fragment patterns, GAs are particularly suited to use in experimental conditions where variations in velocity may exceed 5%.

The conceptual basis of GAs is Darwinian "survival of the fittest." In nature, individuals compete for resources (e.g., food, shelter, mates, etc.). Those individuals which are most highly adapted for their environment tend to produce more offspring. GAs attempt to mimic this process by "evolving" solutions to problems.

GAs operate on a "population" of individuals, each of which is a possible solution to a given problem. Each individual in the starting population is assigned a unique binary string which can be considered to represent that individual's "genotype." The decimal equivalent of this binary genotype is referred to as the "phenotype." A fitness function operating on the phenotype reflects how well a particular individual solves the problem.

Figure 6:
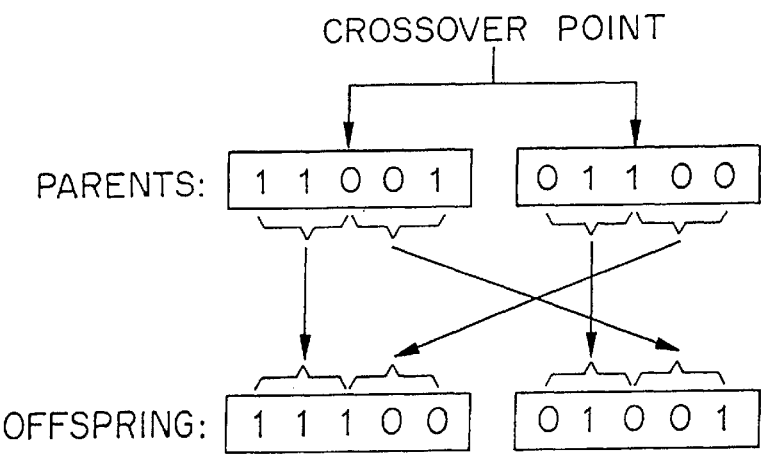
FIG. 6 shows the process of "reproduction" using Genetic Algorithms.

Once the fitness of every individual in the starting population has been determined, a new generation is created through reproduction. Individuals are selected for reproduction from the starting population based on their fitness. The higher an individual solution's fitness, the greater the probability of it contributing one or more offspring to the next generation. During reproduction, the number of individuals in a population is kept constant through all generations. "Reproduction" results from combining the genotypes of the individuals from the prior generation with the highest fitness. Thus, as shown in FIG. 6, in a population of four individuals, portions of the genotype of the two individuals with the highest fitness are exchanged at a randomly selected cross-over point to yield a new generation of off-spring.

A further aspect of the Genetic Algorithm approach is the random use of "mutations" to introduce diversity into the population. Mutations are performed by flipping a single randomly selected bit an individual's genotype.

Arriving at a solution to a problem using GAs involves the repeated steps of fitness evaluation, reproduction (through cross-over), and possibly mutation. Each step is simply repeated in turn until the population converges within predetermined limits upon a single solution to the given problem. A pseudo-code implementation of this process is shown in Table 1.

TABLE 1

Genetic Algorithm in Pseudo-code

```
BEGIN
    generate initial population
    compute the fitness of each individual
    WHILE NOT finished DO
        FOR (population_size / 2) DO
            select two individuals from old generation for
                mating
            recombine the two individuals to create two
                offspring
            randomly mutate offspring
            insert offspring into new generation
        END
        IF population has converged THEN
            finished := TRUE
        END
END
```

Beasley et al., "An Overview of Genetic Algorithms: Part 1, Fundamentals", University Computing 15(2): 58–69 (1993).

It will be appreciated by persons skilled in the art that the task of aligning fragment patterns needs to take into account a great many experimental variations, including variations in sample preparation chemistry; sample loading; gel material; gel thickness; electric field density; clamping/securing of gel in instrument; detection rate and other aspects of the electrophoresis process. We have found experimentally that applying a second-order polynomial $$f(x)=c+bx+ax^2$$

where c reflects the linear shift, b reflects the stretch or shrink, and a reflects the rate at which this stretch or shrink occurs to a clean fragment pattern provides good normalization of the clean fragment pattern with a standard fragment pattern for experimental data having variations in velocity of up to 45%. Using GAs, the coefficients a, b, and c can be readily optimized.

Figure 7:
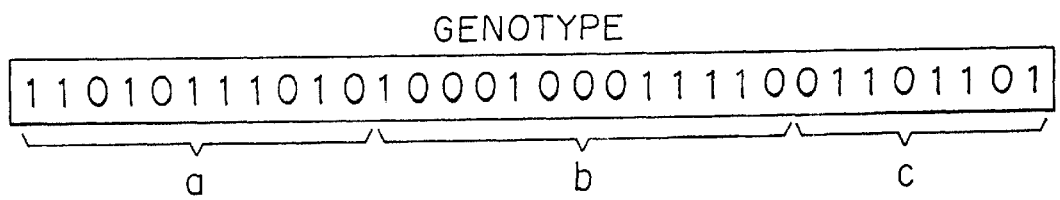
FIG. 7 shows a binary genotype useful for finding values for the coefficients of a second-order polynomial using Genetic Algorithms.

A suitable approach to this optimization uses a binary string as the genotype for each individual, which is divided into three sections representing the three coefficients as shown in FIG. 7. The size of each section is dependent on the range of possible values of each coefficient and the resolution desired. The phenotype of the individual is determined by decoding each section to the corresponding decimal value.

As shown in FIG. 7, a binary string for use in solving the problem presented by this invention may contain 32 bits of which 8 bits specify the offset coefficient c, 13 bits specify the relative velocity b, and 11 bits specify the relative acceleration a. The objective function used to measure the fitness of an individual is the intersection of the standard fragment pattern and an experimental fragment pattern produced by applying the second-order polynomial to the experimental fragment pattern. The intersection is defined by the equation $$f(x, y) = \sum_{i=0}^{n} \min(x_i, y_i)$$

where x is the experimental fragment pattern, y is the standard fragment pattern and n is the number of data points. The intersection will be greatest when the two sequences are perfectly aligned.

Calculating the fitness of each individual is a three step process. First the individual's genotype is decoded producing the values (phenotypes) for the three coefficients. Second, the coefficients are plugged into the second-order polynomial and the polynomial is used to modify the clean fragment pattern. Third, the intersection of the modified fragment pattern and the standard pattern is calculated. The intersection value is then assigned to the individual as its fitness value. About 20 generations are needed to align the two sequences using a population of 50 individuals with a mutation probability of 0.001 (i.e. 1 out of every 1000 bits mutated after crossover). Using conventional computer equipment this can be accomplished in approximately 8 seconds. This time period is sufficiently short that all calculations can be run for a standardized period of time, rather than to a selected degree of convergence. This substantially simplifies experimental design.

Occasionally, the second-order polynomial will be unable to normalize the two sequences. This is due to variations in the velocity of the experimental fragment pattern which are greater than second-order. This is easily handled by using a higher order polynomial, for example a third-or fourth-order polynomial, and a larger binary genotype to include the extra coefficients; or by simply dividing the experimental fragment pattern into segments or windows such that each segment's variations are at most second-order.

Once normalized fragment patterns have been obtained, they may be used in various ways including base-calling and mutation detection. For purposes of determining the complete sequence of all four bases in the sample polymer, this will generally involve the superposition of the normalized fragment patterns for each of the four bases. This can be done by designating a starting point or other "alignment point" in each fragment, and aligning those points to position the aligned fragment patterns. Alternatively, the fragments can be aligned using a reference peak as disclosed in U.S. patent application Ser. No. 08/452,719, now U.S. Pat. No. 5,786,142 filed May 30, 1995, which is incorporated herein by reference.

Figure 8:
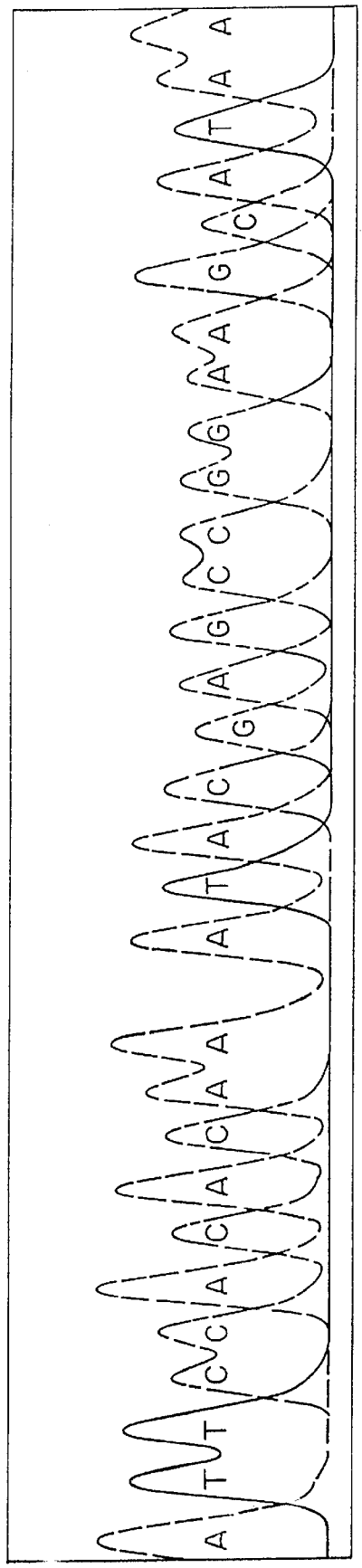
FIG. 8 illustrates the exercise of base-calling of aligned data, as obtained from a Pharmacia A.L.F.(tm) and processed using HELIOS (tm) software.

FIG. 8 illustrates the exercise of base-calling of aligned data, as obtained from a Pharmacia A.L.F. Sequencer and processed using HELIOS (tm) software. Such base-calling may be by any method known in the prior art, using aligned fragment patterns for each of the four bases to provide a complete sequence.

Generally in base-calling, there are two steps, peak detection and sequence correlation. The minimum value used in peak detection varies with each sequence and must be set on a per-run basis. The well-known Fast Fourier Transform version of correlation is used to speed its calculation.

Once the peak maxima are identified and located in time, potential ambiguities are identified. Absent any potential ambiguities, a sequential record of the nucleotide represented by each sequential peak concludes the base-calling exercise. In the diagnostic environment to which the present application applied, however, the nucleotide sequence record can be utilized to detect specific mutations. This can be accomplished in a variety of ways, including amino acid translation, identification of untranslated signal sequences such as start codons, stop codons or splice site junctions. A preferred method involves determining correlations of the normalized fragment patterns against a standard to obtain specific diagnostic information about the presence of mutations.

To perform this correlation, a region around each identified peak in the standard fragment pattern is correlated with the corresponding region in the normalized fragment pattern. After normalization, the correlation will be low in locations where the two sequences differ, i.e., where there is a nucleotide variation because of the high degree of alignment which normalization makes possible. However, correlation of a region extending approximately 20 data points on either side of a peak is desirable to compensate for small discrepancies which may remain. The correlation process is then repeated for each peak in the normalized fragment pattern. Instances of low correlation for any peak are indicative of a mutation.

The correlation of the peaks of the normalized fragment pattern with the standard fragment pattern can be performed in several ways. One approach is to determine a standard correlation, using the equation for correlation shown above. When two discrete functions are correlated in this manner, a single number is obtained. This number ranges in value from zero to some arbitrarily large number the value of which depends upon the two functions being correlated, but which is not predictable a priori. This can create a problem in setting threshold levels defining high versus low correlation. It is therefore preferable to use a measure of correlation which has defined limits to the range of possible values.

One such measure of correlation is called the "coefficient of correlation" which can be calculated using the formula $$p(f, g) = \frac{\sum_{i=1}^{n} (f_i - f_{mean}) * (g_i - g_{mean})}{(f_{std} * g_{std})}$$

where $f_{std}$ is the standard deviation of function f, and $g_{std}$ is the standard deviation of function g. In this case, the output is normalized to a value of between −1 and 1, inclusively. A value of 1 indicates total correlation, and a value of −1 indicates complete non-correlation. Using this method, a gradient of correlation is supplied, and values which are above a pre-defined threshold, i.e., 0.8, could be flagged as suspect.

An alternative to determining the coefficient of correlation is to use the function $$f(x, y) = \sqrt{\sum_{i=1}^{n} x_i^2 * \sum_{i=1}^{n} y_i^2}$$

where x and y are the data points of the two fragment patterns being compared. This equation provides only a rough correlation value, but relies on little computation to do so. Given the large values frequently encountered, the error in this equation may be acceptable.

To return to the advantages of the invention, it is also noted that use of the standard fragment pattern allows the resolution of nucleotide sequence where ambiguities occur, such as compressions and loss of single nucleotide resolution. Thus, the present invention permits automated analysis of many of the ambiguities which are simply rejected as uninterpretable using by known sequencing techniques and equipment.

It is found experimentally that it is not always necessary to obtain precise signal maxima for each nucleotide in order to determine the presence or absence of mutation in the patient sample. Localized areas which fail to clearly resolve into peaks under high speed electrophoresis can still carry enough wave form information to allow accurate interpretation of the presence or absence of mutation in the patient sample when the sample fragment pattern has been normalized in accordance with the invention.

"Compressions" are localized areas of fragment pattern anomalies wherein a series of bands in aligned data are not separated to the same degree as other nearby bands. Compressions are thought to result from short hairpin hybridizations at one end of the nucleic acid molecule which tend to cause a molecule to travel faster through an electrophoresis gel than would be expected on the basis of size. The resulting appearance in the fragment pattern is illustrated in FIG. 9. These compressions may consist of overlapping peaks within one lane that give one large peak, or, they may be peaks from different lanes that overlap when combined together in the alignment process.

Normally, a base-calling method is not able to determine the number or order of the bases in the compression, because it is unable to distinguish the correct ordering of bands. Examination reveals a peak (Peak A) which is clearly wider than a singleton peak (Peaks B and C) but is otherwise indefinable. The method and system of the instant invention, however, assigns the correct order and the correct number of nucleotides based on what is known about the standard fragment pattern.

As stated hereinabove, the standard fragment pattern includes regions of compressions that are typical of a given nucleotide sequence. A compression can be characterized by the following features (FIG. 9): Peak Height (Ph)

Peak Width at half Ph (Pw)

Peak Area (Pa, not shown)

Centering of Ph on Pw (Cnt, not shown)

A compression is characterized in the trial runs by these features, and the ratios between the features. An average and standard deviation is calculated for each ratio. The more precise and controlled the trial runs have been, the lower the standard deviation will be. The inclusiveness of the standard deviation must be broad enough to encompass the degree of accuracy sought in base-calling. A standard deviation which includes only 90% of samples, will permit miscalling in 10% of samples, a number which may or may not be too high to be usefully employed. Once ascertained, the compression statistics are recorded in association with the ambiguous peak. These statistics are associated with each compression and herein called a "standard compression."

Each standard compression can be assigned a nucleotide base sequence upon careful investigation. Researchers resolve compressions by numerous techniques, which though more cumbersome or less useful, serve to reveal the actual underlying nucleotide sequence. These techniques include: sequencing from primers nearer to the compression, sequencing the opposite strand of DNA, electrophoresis in more highly denaturing conditions, etc. Once the actual base sequence is determined, it can be assigned as a group to the compression, thus relieving the researcher from further time consuming exercises to resolve it.

Regions of the normalized fragment patterns which do not show discrete peaks for base-calling are tested for the existence of known compressions. If no compression is known for the region, the area is flagged for the human operator to examine as a possible new mutation.

Figure 9A:
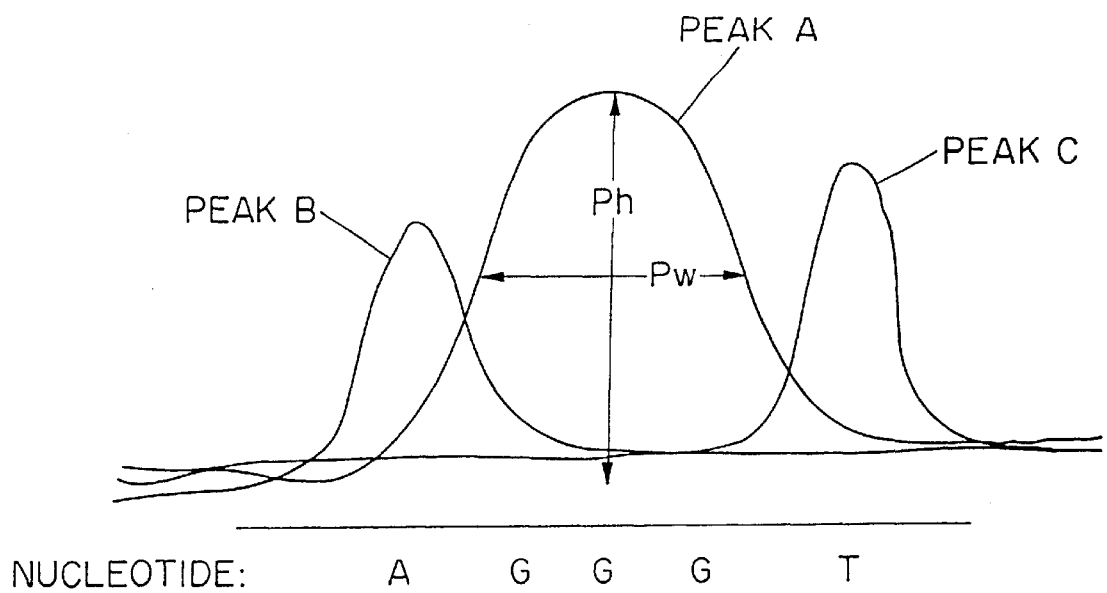
FIGS. 9A and 9B illustrate a sequencing compression.
Figure 9B:
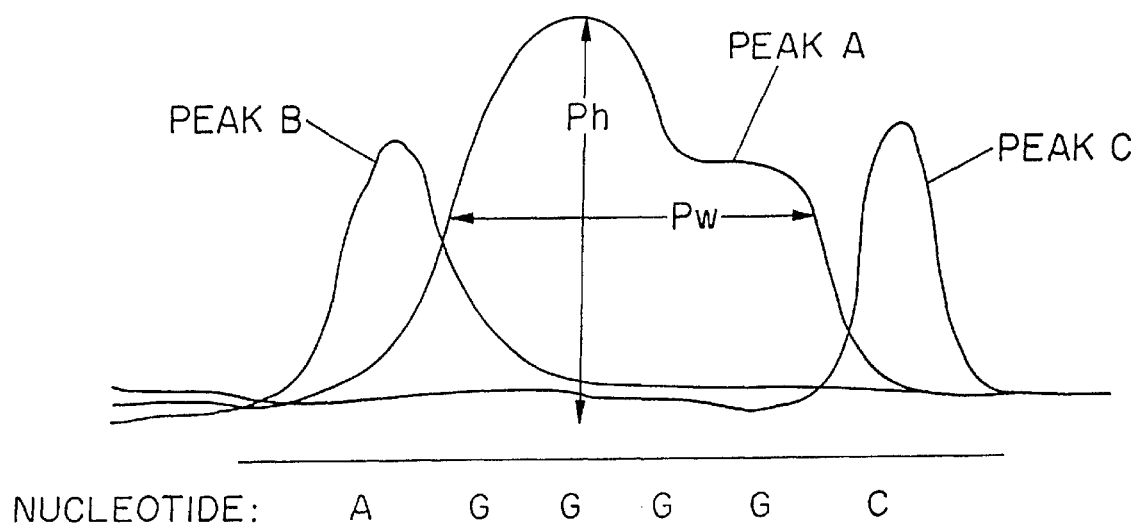

On the other hand, if the locus of the peak indicates that it lies in a region of known compression, the ratios of the peak are determined as above. If the peak falls within the standard deviation of all the ratios determined from the trial runs, it is then assigned the sequence of the standard compression. FIGS. 9A and 9B identify the actual nucleotides assigned to a standard compression.

Where, however, the ratios determined for the compression fall outside of the standard deviation, there lies the possibility of mutation. In this case, the ratios of the compression are compared to all known and previously observed mutations in the standard compression. If the compression falls within any of the previously identified mutations in the region, it may be identified as corresponding to such a mutation. If the ratios fall outside of any known standard, the area is flagged for examination by the human operator as an example of a possible new and hitherto unobserved mutation.

A further application of the present invention is for base-calling beyond the limits of single nucleotide resolution. In this case, the standard fragment pattern will define a region where single nucleotide resolution is not observed. In cases of poor sequencing conditions and a weakly resolving apparatus, resolution may fail around 200 nts. In excellent conditions, some apparatus are known to produce read-lengths of over 700 nts. In either case, there is a point which single nucleotide resolution is lost and base-calling cannot be performed accurately.

The instant invention relies on normalization using a standard fragment pattern to resolve the ambiguous wave forms beyond the limit of single nucleotide resolution. The method is essentially the same as a series of compression analyses as described hereinabove. The wave forms beyond the limit of resolution in the standard fragment pattern are measured and ratios between all features are calculated, to create an extended series of standard peaks. Normalized fragment patterns, prepared as described hereinabove, may be sequentially analyzed for consistency with the expected ratios of each peak-like feature. Any wave form which does not fall within the parameters of the standard peaks is classified as anomalous and flagged for further investigation.

As noted above, in some applications of the invention it is not necessary to perform base-calling for all four nucleotide-specific channels in order to detect mutations. According to the instant invention, it is possible to compare any base specific experimental fragment pattern, for example the T lane of the patient sample, to the base specific standard fragment pattern for that T lane. The features of the standard fragment pattern can be used to identify differences within the test lane of the sample and thus provide information about the sample.

Figure 10:
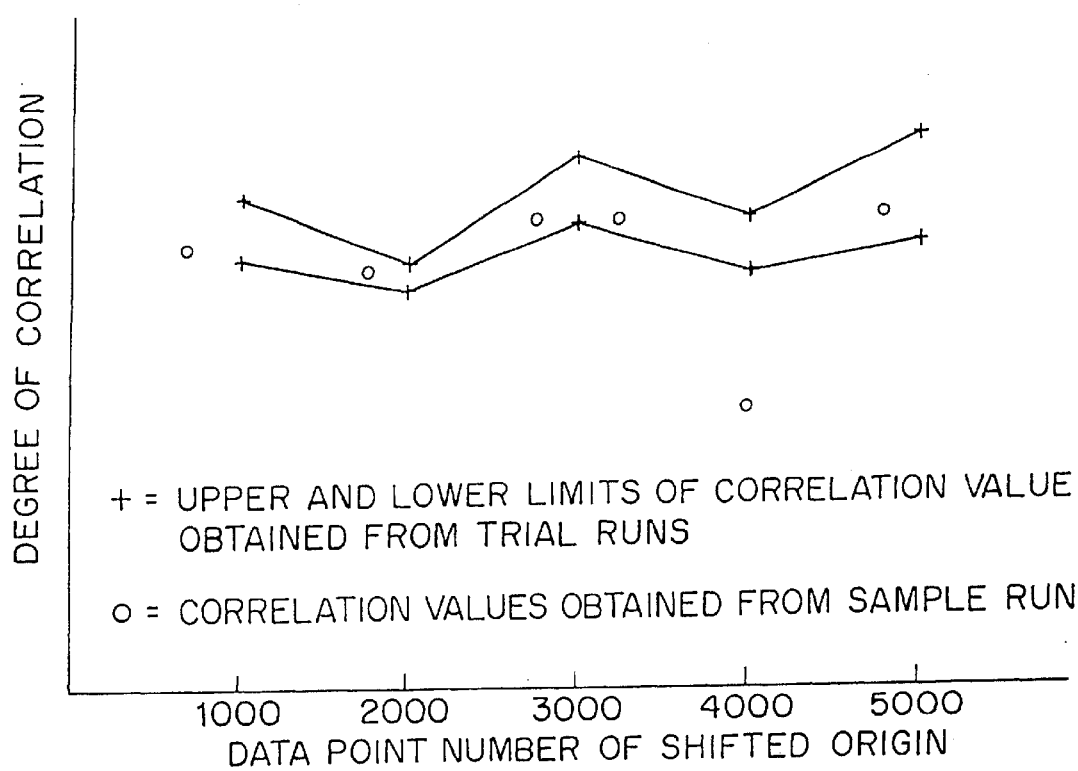
FIG. 10 illustrates a cross correlogram which plots maximum correlation against data point number of shifted Origin across the entire length of sample and standard fragment patterns.

This aspect of the invention follows the normalization step described hereinabove. The degree of correlation of a window at the preferred normalization is plotted against the shifted origin data point of the window, effectively describing a cross-correlogram. FIG. 10 shows the maximum and minimum correlation values obtained across the entire length of the standard fragment pattern, as determined from a plurality of trial runs. A standard deviation can be determined after a sufficient number of trial runs. Data from a test sample is also plotted. As illustrated, one window is found to deviate substantially from its expected degree of correlation. The failure to correlate as expected suggests that the window contains a mutation or other difference from the standard. The system of the invention would cause such a window to be flagged for closer examination by the human operator. Alternatively, the window could be reported directly to the patient file for use in diagnosis. In a further alternative, the window would not be reported to the human operator, until base-calling had further confirmed that there was a mutation present in the area represented by the window.

In general, the cross correlogram mutation detection is a method of "single lane base-calling" wherein the signal from a single nucleotide run is used to identify the presence or absence of differences from the standard fragment pattern. A useful embodiment of this aspect of the invention is for identification of infectious diseases in patient samples. Many groups of diagnostically-significant bacteria, viruses, fungi and the like all contain regions of DNA which are unique to an individual species, but which are nevertheless amplifiable using a single set of amplification primers due to commonality of genetic code within related species. Diagnostic tests for such organisms may not quickly distinguish between species within such groups. Using the method of the invention, however, it is possible to quickly classify a sample as belonging to one species within a group on the basis of the standard fragment patterns for one selected type of nucleotide. This eliminates the need to base-call four lanes of nucleotides and effectively allows a DNA sequencing apparatus to run four times as many samples in the same time period as before.

Thus, in accordance with the present invention, there is provided a method for classifying a sample of a nucleic acid as a particular species within a group of commonly-amplifiable nucleic acid polymers. The method utilizes at least one sample fragment pattern representing the positions of a selected type of nucleic acid base within the sample nucleic acid polymer. For each commonly-amplifiable species within the group, a set of one or more normalization coefficients is determined for the sample fragment pattern. These sets of normalization coefficients are then applied to the sample fragment pattern to obtain a plurality of trial fragment patterns, which are correlated with the corresponding standard fragment patterns. The sample is classified as belonging to the species for which the trial fragment pattern has the highest correlation with its corresponding standard fragment pattern, provided that the correlation is over a pre-defined threshold.

This aspect of the invention is useful in identifying which allele of a group of alleles is present in a gene. The method is also useful in identifying individual species from among a group of genetic variants of a disease-causing microorganism, and in particular genetic variants of human immunodeficiency virus.

A further variation of the invention which may be useful in certain conditions is the reduction of the experimental and standard fragment patterns into square wave data. Square wave data is useful when the signal obtained is highly reproducible from run to run. The main advantage of a square wave data format is that it includes a maximum of information content and a minimum of noise.

The standard fragment pattern may be reduced to a square wave by a number of means. In one method, the transition from zero to one occurs at the inflection point on each slope of a peak. The inflection points are found by using the zero crossings of a function that is the convolution of the data function with a function that is the second derivative of a gaussian pulse that is about one half the width of single base pair pulse in the original data sequence. This derives inflection points with relatively little addition of noise due to the differentiation process. Any data point value greater than the inflection point on that slope of the peak is assigned 1. Any value below the inflection point is assigned 0.

The peaks on the square wave are identified and assigned nucleotide sequences. Peaks may be assigned one or more nucleotides as determined by the human operator on the basis of the standard fragment pattern. Peaks are then given identifying characteristics such as a sequential peak number, a standard peak width, a standard gap width on either side of the peak and standard deviations with these characteristics.

When a sample fragment pattern is obtained, it is reduced to a square wave format, again on the basis of the inflection point data as described above. Peak numbers are assigned. The sample square wave may then be used in different ways to identify mutations. In one method, it may be used to align the four different nucleotide data streams as in the method of the invention described'hereinabove. Alternatively, analysis may be purely statistical. The peak width and gap width of sample can be directly compared to the standard square wave. If the sample characteristics fall within the standard deviation of the standard, taking into account permissible elasticity of the peaks, then the sample is concluded to be the same as the standard. If the peaks of the sample can not be fit within the terms of the standard, then the presence of a mutation is concluded and reported.

Figure 11:
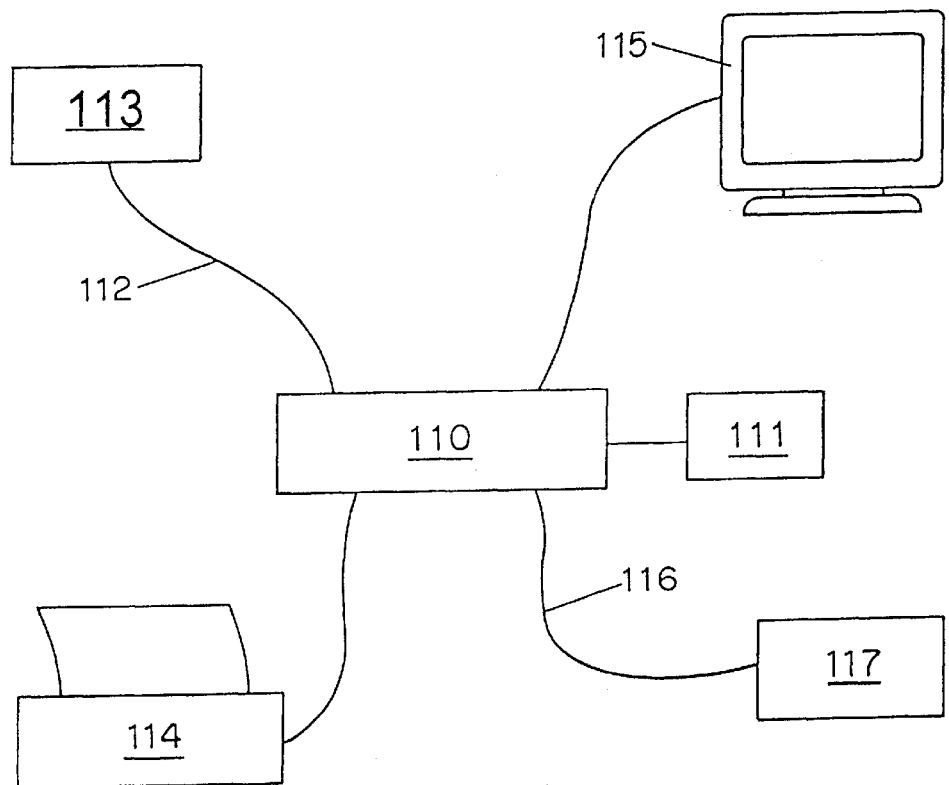
FIG. 11 shows an apparatus in accordance with the invention.

The present invention is advantageously implemented using any multipurpose computer including those generally referred to as personal computers and mini-computers, programmed to determine normalization coefficients by comparison of an experimental and a standard fragment pattern. As shown schematically in FIG. 11, such a computer will include at least one central processor 110, for example an Intel 80386, 80486 or Pentium® processor or Motorola 68030, Motorola 68040 or Power PC 601, a storage device, such as a hard disk 111, for storing standard fragment patterns, means for receiving raw or clean experimental fragment patterns such as wire 112 shown connected to the output of an electrophoresis apparatus 113.

The processor 110 is programmed to perform the comparison of the experimental fragment pattern and the standard fragment pattern and to determine normalization coefficients based on the comparison. This programming may be permanent, as in the case where the processor is a dedicated EEPROM, or it may be transient in which case the programming instructions are loaded from the storage device or from a floppy diskette or other transportable media.

The normalization coefficients may be output from computer, in print form using printer 114; on a video display 115; or via a communications link 116 to another processor 117. Alternatively or additionally, the normalization coefficients may be utilized by the processor 110 to normalize the experimental fragment pattern for use in base-calling or other diagnostic evaluation. Thus, the apparatus may also include programming for applying the normalization coefficients to the experimental fragment pattern to obtain a normalized fragment pattern, and for aligning the normalized fragments patterns and evaluating the nucleic acid sequence of the sample therefrom.

We claim:

1. An apparatus for normalizing an experimental nucleic acid fragment pattern putatively representing a known nucleic acid sequence comprising:
    (a) a computer processor;
    (b) a storage device having stored thereon a standard fragment pattern for a nucleic acid polymer actually having the known sequence;
    (c) a computer program means for receiving the experimental nucleic acid fragment pattern; and
    (d) means for causing the computer processor to determine one or more normalization coefficients for the experimental fragment pattern, said normalization coefficients being selected to provide a high degree of overlap between a normalized fragment pattern obtained by applying the normalization coefficients to the experimental fragment pattern and the standard fragment pattern.

2. An apparatus according to claim 1, wherein the means for causing the computer processor to determine one or more normalization coefficients is a program stored on the storage device.

3. An apparatus according to claim 2, wherein the normalization coefficients are coefficients of a second-or higher-order polynomial.

4. An apparatus according to claim 3, wherein the normalization coefficients are determined using Genetic Algorithms.

5. An apparatus according to claim 1, wherein the normalization coefficients are determined using Genetic Algorithms.

6. An apparatus according to claim 1, further comprising means for applying the normalization coefficients to the experimental fragment pattern to obtain a normalized fragment pattern.

7. An apparatus according to claim 6, further comprising means for aligning the normalized fragments patterns and evaluating the nucleic acid sequence of the experimental fragment pattern therefrom.

8. An apparatus according to claim 1, further comprising an electrophoresis apparatus, operatively coupled to the means for receiving an experimental fragment pattern.

9. An apparatus according to claim 8, wherein the means for causing the computer processor to determine one or more normalization coefficients is a program stored on the storage device.

10. An apparatus according to claim 8, wherein the normalization coefficients are coefficients of a second-or higher-order polynomial.

11. An apparatus according to claim 10, wherein the normalization coefficients are determined using Genetic Algorithms.

12. An apparatus according to claim 8, wherein the normalization coefficients are determined using Genetic Algorithms.

13. An apparatus according to claim 8, further comprising means for applying the normalization coefficients to the experimental fragment pattern to obtain a normalized fragment pattern.

14. An apparatus according to claim 13, further comprising means for aligning the normalized fragments patterns and evaluating the nucleic acid sequence of the experimental fragment pattern therefrom.

* * * * *